United States Patent
Lin et al.

(10) Patent No.: US 10,526,369 B2
(45) Date of Patent: Jan. 7, 2020

(54) OXIDATIVE MODIFICATION IMPROVES THE DRUGABILITY OF CELL PENETRATING PEPTIDES AS DRUG CARRIERS

(71) Applicant: JOWIN BIOPHARMA, New Taipei (TW)

(72) Inventors: Yu-Min Lin, Taipei (TW); Wei-Chen Chen, Taichung (TW); Win-Chin Chiang, New Taipei (TW); Ting Lian Chang, Kaohsiung (TW); Chun-Hung Kuo, New Taipei (TW)

(*) Notice: Subject to any disclaimer, the term of this patent is extended or adjusted under 35 U.S.C. 154(b) by 0 days.

(21) Appl. No.: 15/480,414

(22) Filed: Apr. 6, 2017

(65) Prior Publication Data
US 2018/0105556 A1 Apr. 19, 2018

Related U.S. Application Data

(60) Provisional application No. 62/407,540, filed on Oct. 13, 2016.

(51) Int. Cl.
| | | |
|---|---|---|
| *C07K 7/06* | (2006.01) | |
| *C07K 14/47* | (2006.01) | |
| *A61K 31/727* | (2006.01) | |
| *A61K 38/00* | (2006.01) | |

(52) U.S. Cl.
CPC .............. *C07K 7/06* (2013.01); *A61K 31/727* (2013.01); *C07K 14/47* (2013.01); *A61K 38/00* (2013.01); *C07K 2319/10* (2013.01)

(58) Field of Classification Search
CPC . A61K 38/00; A61L 2300/404; G01N 33/574
See application file for complete search history.

(56) References Cited

U.S. PATENT DOCUMENTS

| | | |
|---|---|---|
| 7,595,374 B1 | 9/2009 | Chang et al. |
| 8,372,951 B2 | 2/2013 | Chang et al. |
| 2010/0016239 A1 | 1/2010 | Chang et al. |
| 2013/0315828 A1 | 11/2013 | Chang et al. |

OTHER PUBLICATIONS

Chen et al. "A Heparan Sulfate-Binding Cell Penetrating Peptide for Tumor Targeting and Migration Inhibition", Hindawi Publishing Corporation, vol. 2015, Nov. 14, 2014.
Kristensen et al. "Applications and Challenges for Use of Cell-Penetrating Peptides as Delivery Vectors for Peptide and Protein Cargos", Molecular Sciences, Jan. 30, 2016.
Fang et al. "A Novel Cell-Penetrating Peptide Derived from Human Eosinophil Cationic Protein", Plos One, vol. 8, Issue 3, Mar. 4, 2013.
Lu, Jia-Yin. "Nuclear Magnetic Resonance study of heparin enhanced micelle interaction on novel cell-penetrating peptide, ECP32-41", Master Thesis, National Tsing Hua University, 2015.
Schinzel et al, "The phosphate recognition site of *Escherichia coli* maltodextrin phosphorylase", Elsevier B.V.,vol. 286, Issues 1-2, pp. 125-128, Jul. 29, 1991.
Lien et al, "In Silico Prediction and In Vitro Characterization of Multifunctional Human RNase3", Hindawi, vol. 2013, Dec. 2012.
Chen et al, "A Heparan Sulfate-Binding Cell Penetrating Peptide for Tumor Targeting and Migration Inhibition", Hindawi, vol. 2015, Nov. 2014.

*Primary Examiner* — Soren Harward
*Assistant Examiner* — Jia-Hai Lee

(57) ABSTRACT

The present invention provides a cell penetrating peptide dimer by oxidative modification, in which each monomer is connected with each other by the disulfide linkage. The drugability of the peptide dimer has been improved through enhancing stability, reducing proteolysis, retaining permeability and increasing heparan sulfate binding specificity. The modified peptide products can be used to deliver drug molecules as a suitable drug carrier for targeted therapy.

9 Claims, 7 Drawing Sheets

Specification includes a Sequence Listing.

OXIDATIVE MODIFICATION IMPROVES THE DRUGABILITY OF CELL PENETRATING PEPTIDES AS DRUG CARRIERS

BACKGROUND OF THE INVENTION

1. Field of the Invention

The present invention relates to a cell penetrating peptide produced by oxidative modification. In particular, it relates to a cell penetrating peptide dimer having disulfide linkage. This dimer improves past characteristics of the cell penetrating peptide, and especially for improving the problem of drug stability when applied in drug carriers.

2. Description of the Related Art

One major problem in chemotherapy of cancer treatment is non-selective toxicity, which causes undesirable side effects, a narrow therapeutic window and a compromised clinical prognosis, because drugs do not identify differences between normal cells and cancer cells. In order to reduce damages to normal tissues, sub-optimal doses are often administered for anticancer chemotherapeutics, but the desired effects cannot be achieved. For circumventing those challenges, targeted drug delivery systems hold significant promise to improve drug efficacy and lower side effects by enabling the drug to a specific cell type. To date, many researches show that monoclonal antibodies, peptides, proteins, and small molecules have been used to selectively bring drugs to cancer cells with upregulated receptors by forming carrier-drug conjugates. However, none of the carrier-drug conjugates produced by peptides has successfully launched. This may be due to several reasons including (a) the difficulty in discovering the appropriate ligand matched for the targeted receptors on the cell surface; (b) the lack of information on the mechanisms of uptake and elimination of the ligand inside the cells, and (c) the limited number of systematic studies on the relationships between the physicochemical and transport properties of the conjugates.

Recently, the discovery of a new cell penetrating peptide (CPP) may contribute some ideas to solve those problems mentioned above. This peptide, $CPP_{ecp}$, derived from the region of human eosinophil cationic protein [ECP(32-41)]. It has previously been proven that the motif located within the $CPP_{ecp}$ shows heparin or heparan sulfate binding activity and the $CPP_{ecp}$ exhibits low cell toxicity, moderate migration inhibition to cancer cell, and highly cell-penetrating efficacy through macropinocytosis. Such functional characteristics of $CPP_{ecp}$ have brought itself to the claim to be a drug carrier for medication.

However, in general, natural peptides tend to have relatively short circulating plasma half-lives, low permeability and metabolic instability, leading to limited residence time in tissues. Even if $CPP_{ecp}$ has been approved for the highly cellular permeability, short half-life is still a challenge for itself to become successful drug carriers due to multiple absorption, distribution, metabolism, and excretion (ADME) issues. In the present invention, strategies developed to improve peptide drugability through enhancing stability, reducing proteolysis, retaining permeability and increasing selective heparan sulfate binding activity are disclosed.

The above information disclosed in this section is only for enhancement of understanding of the background of the described technology and therefore it may contain information that does not form the prior art that is already known to a person of ordinary skill in the art.

SUMMARY OF THE INVENTION

The present invention offers a concept to improve peptide drugability of a cell penetrating peptide, which is called $CPP_{ecp}$ having following sequence: $NYBX_1BX_2BNQX_3$, (SEQ. ID NO:1) wherein B represents a basic amino acid, $X_1$ represents an amino acid with an aromatic, a hydrophobic or an uncharged side chain, $X_2$ represents C, and $X_3$ represents N or none.

To achieve above-mentioned objective, the present invention further provides strategies to improve peptide drugability through enhancing peptide stability, reducing proteolysis, retaining permeability and increasing selective heparan sulfate binding activity.

The present invention provides another method for intracellular delivery, comprising: (a) providing a complex including the aforementioned cell penetrating peptide; and (b) culturing the complex with a targeted cell.

The present invention also provides a complex, which comprises the modified drug carrier disclosed in the present invention and one to two cargos selected from the group consisting of therapeutic agents, diagnostic probes, peptides, nucleic acids, antisense oligonucleotides, proteins, nanoparticles, liposomes, small molecules and radioactive materials for single or combination therapy.

The present invention also provides a method for delivering the desired cargo(s) into a subject comprising: (a) preparing a complex comprising the modified drug carrier disclosed in the present invention and the desired cargo(s), and (b) orally, intraarticularly, intraperitoneally, intrathecally, intrarterially, intranasally, intraparenchymally, subcutaneously, intramuscularly, intravenously, dermally, intrarectally, or topically administering the complex to a subject.

The advantage of the present invention is able to be applied in combinational therapy or theranostics.

Many of the attendant features and advantages of the present invention will becomes better understood with reference to the following detailed description considered in connection with the accompanying drawings.

BRIEF DESCRIPTION OF THE DRAWINGS

The detailed structure, operating principle and effects of the present invention will now be described in more details hereinafter with reference to the accompanying drawings that show various embodiments of the present invention as follows.

DETAILED DESCRIPTION OF THE INVENTION

Figure 1:
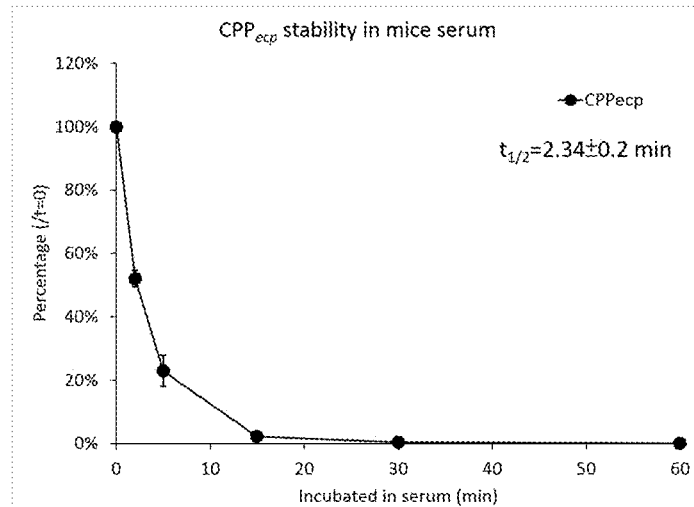
FIG. 1 illustrates the stability of $CPP_{ecp}$ in mice serum. $CPP_{ecp}$ was dissolved in 1× PBS (4 mg/ml) and incubated with equal volume of mice serum (final 50%) for different time points (0, 2, 5, 15, 30, 60 min, respectively). The reaction was terminated by the addition of an equal volume of TCA solution (final 50%) and denatured serum proteins were removed by centrifugation. The supernatant was then assayed by HPLC to quantify the remaining $CPP_{ecp}$. Zero time point was set as 100 percent of remaining $CPP_{ecp}$ and relative amounts of $CPP_{ecp}$ in each time point were calculated. Data represent the mean±SD (standard deviation) of three independent experiments. The $t_{1/2}$ of $CPP_{ecp}$ was calculated by CompuSyn.

Reference will now be made in detail to the exemplary embodiments of the present invention, examples of which are illustrated in the accompanying drawings. Therefore, it is to be understood that the foregoing is illustrative of exemplary embodiments and is not to be construed as limited to the specific embodiments disclosed, and that modifications to the disclosed exemplary embodiments, as well as other exemplary embodiments, are intended to be included within the scope of the appended claims. These embodiments are provided so that this invention will be thorough and complete, and will fully convey the inventive concept to those skilled in the art. The relative proportions and ratios of elements in the drawings may be exaggerated or diminished in size for the sake of clarity and convenience in the drawings, and such arbitrary proportions are only illustrative and not limiting in any way.

For convenience, certain terms employed in the specification, examples and appended claims are collected here. Unless defined otherwise, all technical and scientific terms used herein have the same meaning as commonly understood by one of the ordinary skill in the art to which this invention belongs.

Various embodiments will now be described more fully with reference to the accompanying drawings, in which illustrative embodiments are shown. The inventive concept, however, may be embodied in various different forms, and should not be construed as being limited only to the illustrated embodiments. Rather, these embodiments are provided as examples, to convey the inventive concept to one skilled in the art. Accordingly, known processes, elements, and techniques are not described with respect to some of the embodiments.

The singular forms "a", "and", and "the" are used herein to include plural referents unless the context clearly dictates otherwise.

The following descriptions are provided to elucidate the process of preparing cell penetrating peptide dimer and to aid it of skilled in the art in practicing this invention. These Examples are merely exemplary embodiments and in no way to be considered to limit the scope of the invention in any manner.

EXAMPLE 1

Improvement of $CPP_{ecp}$ Stabilities

The unmodified $CPP_{ecp}$ (NH2-NYRWRCKNQN-COOH (SEQ. ID NO:2)) was synthesized by MISSION BIOTECH Inc. in TAIWAN. To determine the stability of unmodified $CPP_{ecp}$ in mice serum, 100 μl of $CPP_{ecp}$ (0.5 mg/ml or 4 mg/ml) was mixed with equal volume of whole mice serum (strain: CD-1 (ICR), final 50%) and incubated at room temperature for 0, 2, 5, 15, 30 and 60 min. The reaction was stopped by adding 200 µl of 100% TCA solution and vortexed for 5 seconds to precipitate serum proteins. Denatured serum proteins were removed by centrifugation at 18000 x g, 4° C. for 2 mins. The supernatants were analyzed by HPLC (column: Purospher® STAR RP-18e, eluent A: 0.1% TFA in dH$_2$O, eluent B: 0.1% TFA in acetonitrile, flow rate: 1ml/min, gradient: 2-35% of eluent B in 15 min, UV wavelength: 280 nm). Zero-time point was set as one hundred percent of remaining CPP$_{ecp}$ and relative amount of CPP$_{ecp}$ in each time point were calculated. The $t_{1/2}$ of CPP$_{ecp}$ was calculated by CompuSyn (ver. 1.0). As shown in FIG. 1, the short half-life of unmodified CPP$_{ecp}$ is only 2.34 min in mice serum, which could be the limited issue for future clinical application.

Figure 2:
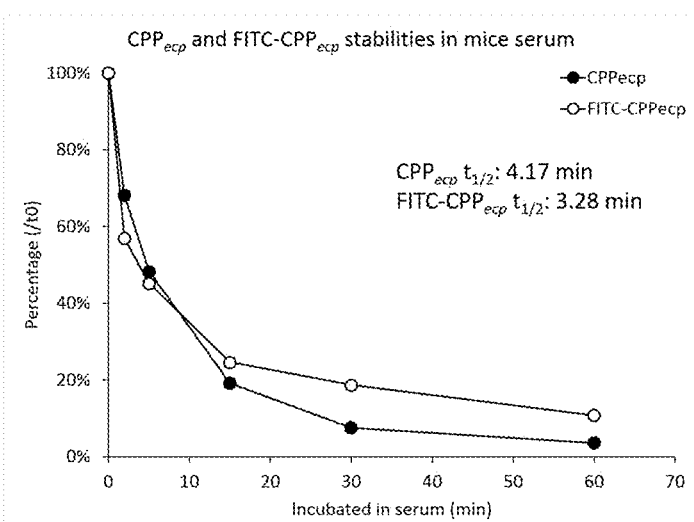
FIG. 2 illustrates comparison of stabilities between $CPP_{ecp}$ and N-terminal FITC-conjugated $CPP_{ecp}$ in mice serum. Both were dissolved in $dH_2O$ (0.5 mg/ml) and incubated with equal volume of 20% mice serum (final 10%) for different time points (0, 2, 5, 15, 30, 60 min, respectively). The reactions were terminated by the addition of an equal volume of TCA solution (final 50%) and denatured serum proteins were removed by centrifugation. The supernatants were assayed by HPLC to quantify the remaining peptides. Zero time point was set as 100 percent of remaining peptides and relative amounts of peptides in each time point were calculated. The $t_{1/2}$ of $CPP_{ecp}$ and N-terminal FITC-$CPP_{ecp}$ were calculated by CompuSyn.
Figure 3:
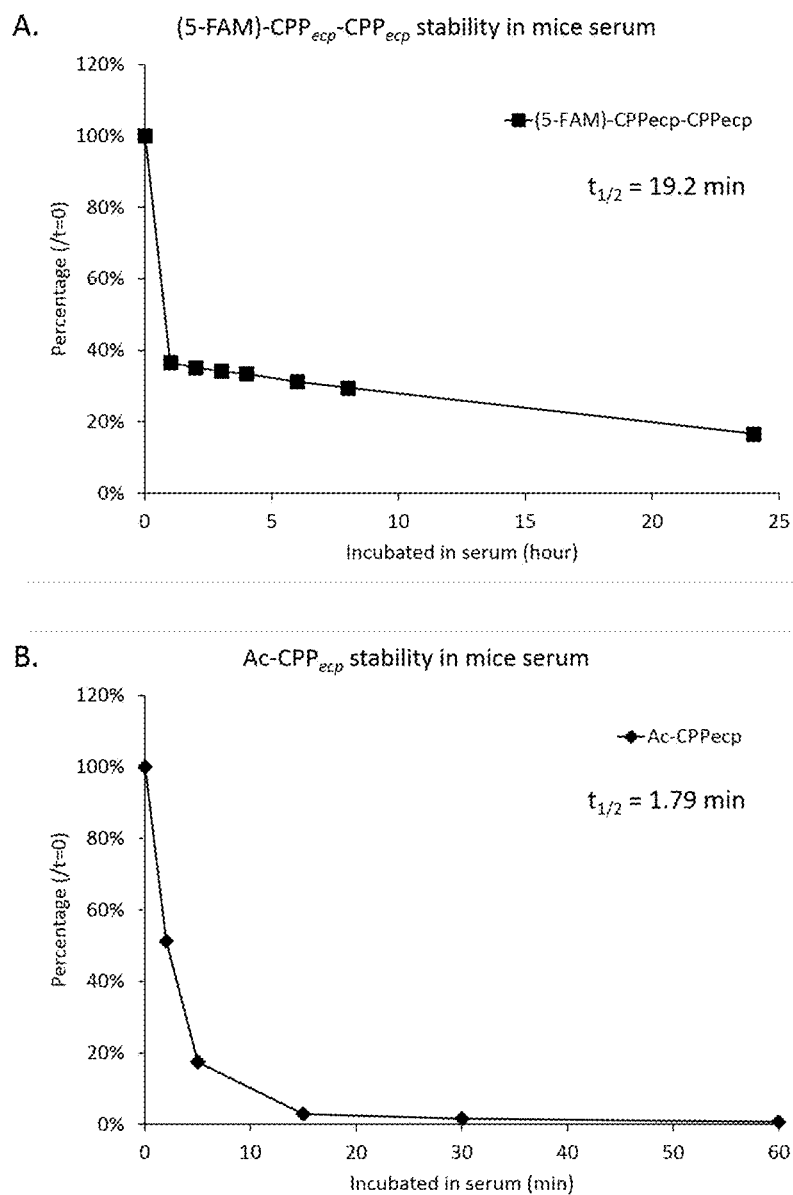
FIG. 3 illustrates stabilities of N-terminal (5-FAM)-$CPP_{ecp}$-$CPP_{ecp}$ (A) and N-terminal Ac-$CPP_{ecp}$ (B) in mice serum. Both modified peptides were dissolved in $dH_2O$ (0.5 mg/ml) and incubated with equal volume of 20% mice serum (final 10%) for different time points (0-24 hours for (5-FAM)-$CPP_{ecp}$-$CPP_{ecp}$ and 0-60 min for Ac-$CPP_{ecp}$, respectively). The reactions were terminated by the addition of an equal volume of TCA solution (final 50%) and denatured serum proteins were removed by centrifugation. The supernatants were assayed by HPLC to quantify the remaining peptides. Zero time point was set as 100 percent of remaining peptides and relative amounts of peptides in each time point were calculated. The $t_{1/2}$ of N-terminal (5-FAM)-$CPP_{ecp}$-$CPP_{ecp}$ and N-terminal Ac-$CPP_{ecp}$ were calculated by CompuSyn.
Figure 5:
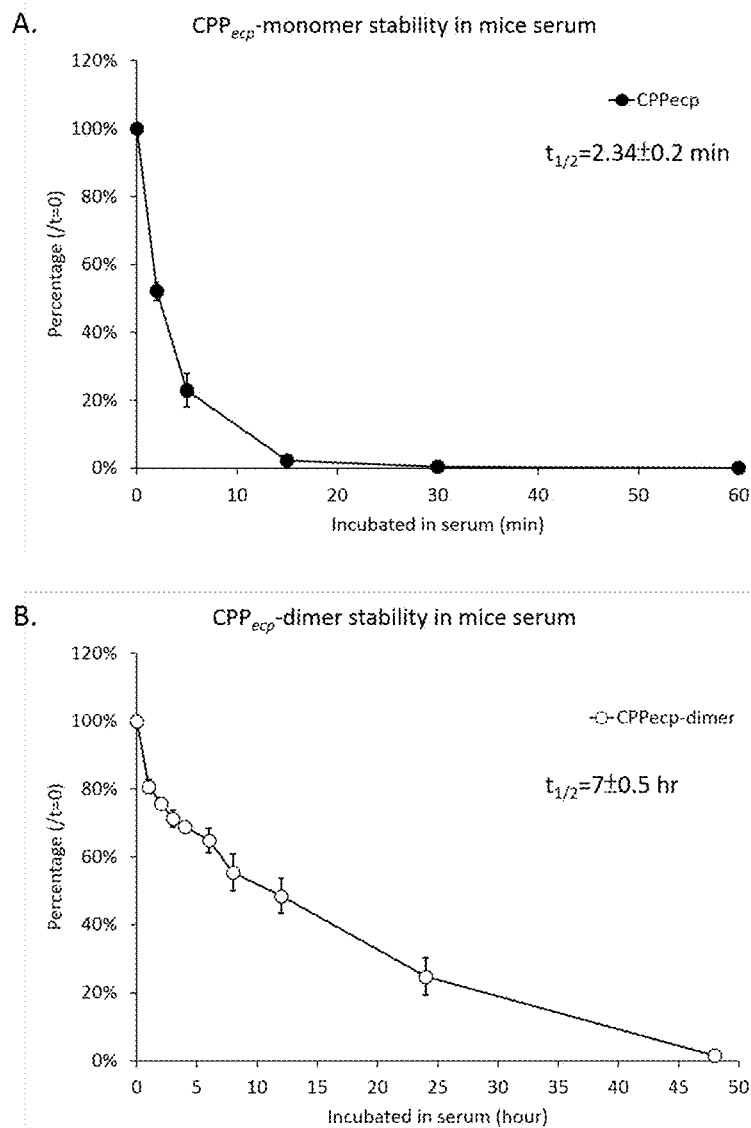
FIG. 5 illustrates comparison of stabilities between $CPP_{ecp}$ (A) and $CPP_{ecp}$-dimer (B) in mice serum. Both peptides were dissolved in 1× PBS (4 mg/ml) and incubated with equal volume of mice serum (final 50%) for different time points (0-60 min for $CPP_{ecp}$ and 0-48 hours for $CPP_{ecp}$-dimer, respectively). The reactions were terminated by the addition of an equal volume of TCA solution (final 50%) and denatured serum proteins were removed by centrifugation. The supernatants were assayed by HPLC to quantify the remaining peptides. Zero time point was set as 100 percent of remaining peptides and relative amounts of peptides in each time point were calculated. Data represent the mean±SD (standard deviation) of three independent experiments. The $t_{1/2}$ of $CPP_{ecp}$ and $CPP_{ecp}$-dimer were calculated by CompuSyn.

As an available drug carrier, proteolytic stability and targeting delivery are two key properties. In order to improve CPP$_{ecp}$ stability, several typical and atypical modifications were introduced and tested including (1) N-terminal fluorescent dye labeling (FITC and 5-FAM) to mimic drug conjugation, (2) N-terminal acetylation (Ac), (3) C-terminal conjugation to another biomolecule, and (4) inter-peptide disulfide bond formation through oxidative modifications. To determine the stabilities of FITC-CPP$_{ecp}$, (5-FAM)-CPP$_{ecp}$-CPP$_{ecp}$ and Ac-CPP$_{ecp}$, 0.5 mg/ml of peptides were dissolved in dH$_2$O, mixed with equal volume of 20% mice serum (final 10%) and analyzed by HPLC as described above. To further determine long-term stabilities, the incubation time was extended (0, 1, 2, 3, 4, 6, 8, 12, 24 and 48 hours). As shown in FIG. 2, compared with unmodified CPP$_{ecp}$, the stability of FITC-CPP$_{ecp}$ was not improved. This result suggests that a simple drug conjugation may not be sufficient to improve the stability of CPP$_{ecp}$ and other strategies are necessary to be explored. In FIG. 3A, N-terminal 5-FAM conjugation and C-terminal elongation of (5-FAM)-CPP$_{ecp}$-CPP$_{ecp}$, indeed, prolonged its stability from 2 to 24 hours. Nevertheless, the dramatic decrease in peptide content within first hour also implies its rapid protein binding in mice serum. On the other hand, N-terminal acetylation, a conventional approach to improve peptide stability, was not sufficient to improve stability of CPP$_{ecp}$ as well (FIG. 3B). However, to our surprise, oxidative modification to form the CPP$_{ecp}$-dimer can increase the stability of CPP$_{ecp}$ up to 180-fold, which indicates the promise of CPP$_{ecp}$-dimer to be a clinical drug carrier (FIG. 5). The half-lives of all modifications compared with CPP$_{ecp}$ were listed in Table. 1 as follows, and $t_{1/2}$ of CPP$_{ecp}$ was set as one-fold.

TABLE 1

| | Modifications | $t_{1/2}$ | Fold increase |
|---|---|---|---|
| CPP$_{ecp}$ | None | 2.34 min | 0 |
| Ac-CPP$_{ecp}$ | N-acetylation | 1.79 min | −24% |
| FITC-CPP$_{ecp}$ | N-terminal FITC conjugation | 3.28 min | +40% |
| (5-FAM)-CPP$_{ecp}$-CPP$_{ecp}$ | N-terminal 5-FAM conjugation and repeated sequences | 19.2 min | +720% |
| CPP$_{ecp}$-dimer | Disulfide linkage | 420 min | +17900% |

Table 1 lists half-lives of CPP$_{ecp}$ with different modifications, including N-terminal protections (linked to FITC and 5-FAM), N-terminal acetylation, C-terminal biomolecular conjugation (conjugated to another CPP$_{ecp}$) and oxidative modification (becoming CPP$_{ecp}$-dimer). The $t_{1/2}$ of CPP$_{ecp}$ was set as one-fold and fold changes of each modified CPP$_{ecp}$ were compared.

EXAMPLE 2

Oxidized Modification of CPP$_{ecp}$ to Form CPP$_{ecp}$-dimer

Figure 4:
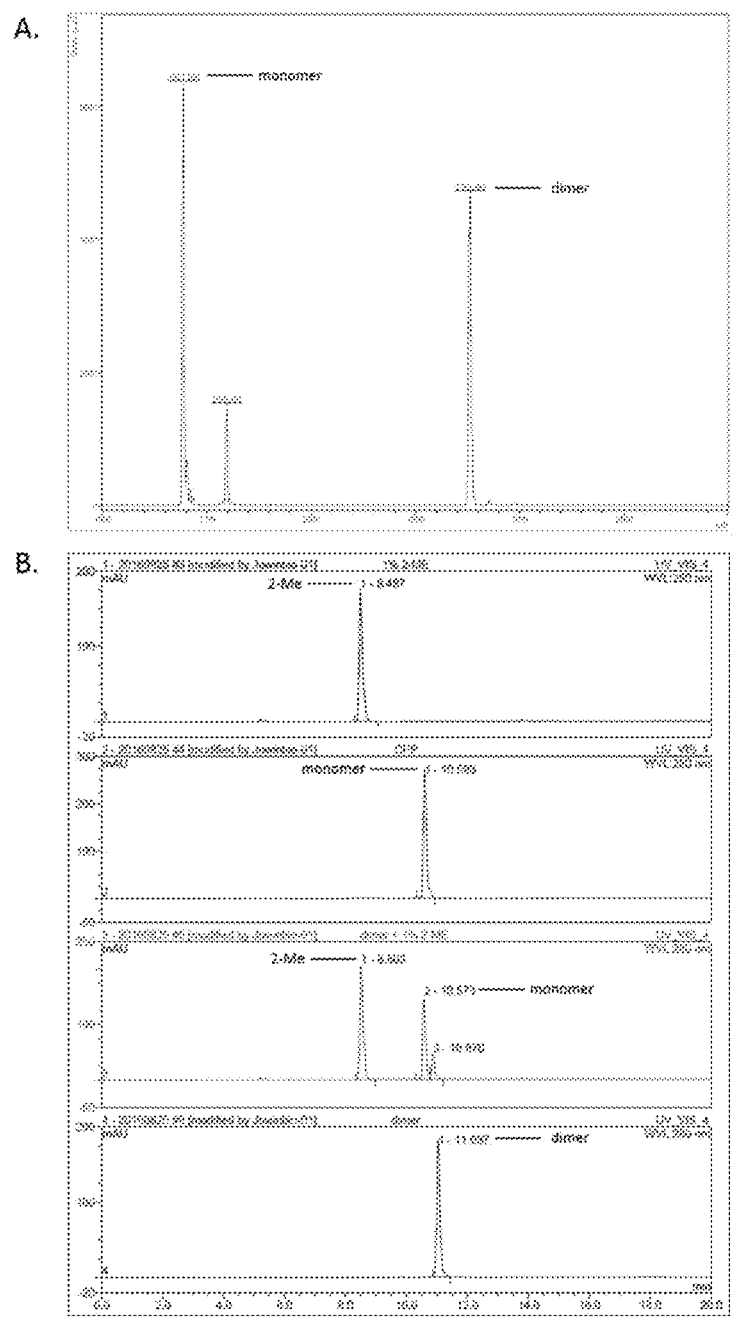
FIG. 4 illustrates molecular mass of $CPP_{ecp}$-dimer (A) and HPLC profiles of 2-mercaptoethanol reduced $CPP_{ecp}$-dimer (B). The cysteine thiol group of $CPP_{ecp}$ was oxidized by 10 mM of $H_2O_2$ or 50 μM of $CuSO_4$ for 12-16 hours. The molecular weight of $CPP_{ecp}$-dimer was determined by MASS spectrometry. In order to confirm the formation of inter-peptide disulfide bond, $CPP_{ecp}$-dimer was incubated with 1% of 2-mercaptoethanol at room temperature for 5 min and analyzed by HPLC. 2-mercaptoethanol was used to reduce disulfide bond to thiol group of cysteine residue.

In order to increase the stability of CPP$_{ecp}$ and improve its application potential, inter-peptide disulfide bond was formed between two cysteine residues in both CPP$_{ecp}$ peptides. For disulfide bond formation, the thiol group of cysteine in CPP$_{ecp}$ was oxidized in the presence of any oxidizing agents, including but not limited to 10 mM H$_2$O$_2$ or 50 µM CuSO$_4$, at room temperature for 12-16 hours to form CPP$_{ecp}$-dimer (Abouelatta, A. I., Campanali, A. A., Ekkati, A. R., Shamoun, M., Kalapugama, S., & Kodanko, J. J. (2009). Oxidation of the natural amino acids by a ferryl complex: kinetic and mechanistic studies with peptide model compounds. Inorganic chemistry, 48(16), 7729-7739.). The CPP$_{ecp}$-dimer was analyzed by HPLC (conditions as described in example 1) and its molecular weight was determined by commercial MASS spectrometry service (MISSION BIOTECH Inc.). For further confirming the inter-peptides disulfide bond formation, CPP$_{ecp}$-dimer was incubated with 1% of 2-mercaptoethanol (SIGMA) at room temperature for 5 min and followed by HPLC analyses. 2-mercaptoechanol was used to reduce disulfide bond to thiol group. As shown in FIG. 4A, the analyzed result of MASS spectrometry was fit for the molecular weight of CPP$_{ecp}$-dimer (molecular weight: 2.76 kDa), which confirmed the formation of CPP$_{ecp}$-dimer. On the other hand, CPP$_{ecp}$-dimer was reduced to monomer by 2-mercaptoehanol, which confirmed the formation of CPP$_{ecp}$-dimer once more (FIG. 4B).

EXAMPLE 3

Cell Surface Binding and Penetration of CPP$_{ecp}$-dimer

Cell Culture

A549 cells were cultured in complete RPMI 1640 medium (Hyclone) supplemented with heated inactivated 10% (v/v) fetal bovine serum (FBS) (Gibco), and 1% (v/v) of penicillin-streptomycin (Gibco). Cells were grown on 15-mm coverslips and incubated at 37° C. in 5% CO$_2$.

Cell Binding and Penetration of CPP$_{ecp}$-dimer

Figure 6:
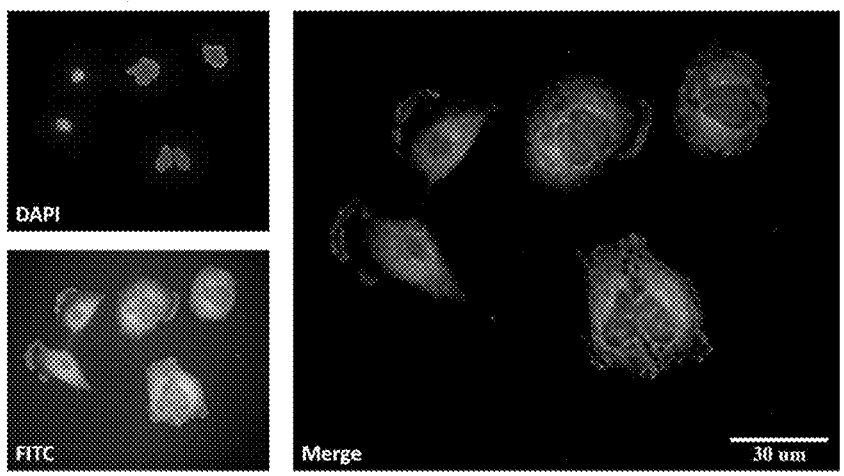
FIG. 6 illustrates cellular uptake of $CPP_{ecp}$ (A) and $CPP_{ecp}$-dimer (B), respectively. Before treatment, each well (12-well plate) was blocked by 2% of BSA for 1 hour, and washed with PBS twice. After blocking, A549 cells were incubated with 12.5 μM of FITC-$CPP_{ecp}$ and FITC-$CPP_{ecp}$ dimer at 37° C. for 30 min. After washing with PBST twice, cells were fixed in methanol for 20 min and washed with PBST four times. The cells were then mounted by DAPI with mounting medium. The binding and penetrating of peptides were analyzed by fluorescence microscopy. Magnification fold: 100×. Scale bar: 30 μm.
Figure 6:
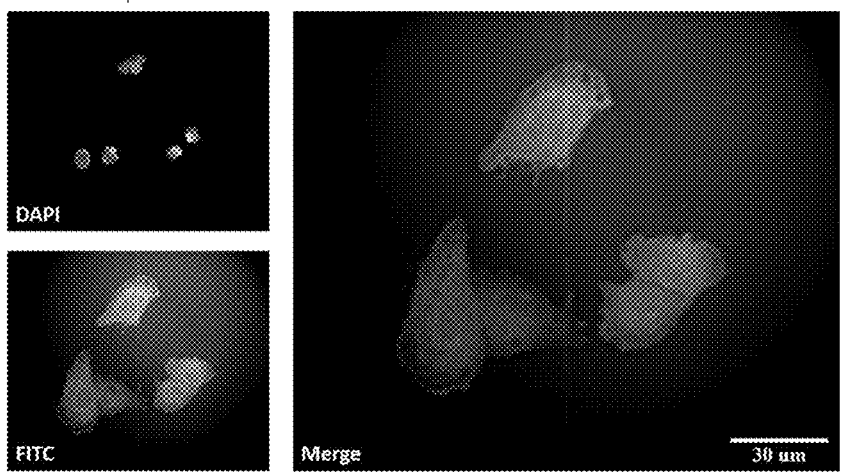

In order to verify if the functionality of disulfide linked dimer of CPP$_{ecp}$ is still maintained as original CPP$_{ecp}$, the abilities of cell binding and penetration were investigated by FITC-conjugated CPP$_{ecp}$ monomer and dimer, and visualized with fluorescence microscopy. Before treatment, each well and inside coverslip of 12-well plate was blocked by 2% BSA for 1 hour to prevent the non-specific binding of peptides, and washed by PBS twice. After blocking, A549 cells grown on 15-mm coverslips were incubated with 12.5 µM of FITC-CPP$_{ecp}$ and FITC-CPP$_{ecp}$-dimer at 37° C. for 30 min. After wash twice in PBST, cells were fixed in methanol for 20 min and washed by PBST four times. The cells were mounted by DAPI containing mounting medium to indicate the nucleus. The binding and penetrating of peptides were analyzed by fluorescence confocal microscopy (Leica) (FIG. 6) (Magnification fold: 100×. Scale bar: 30 µm). As shown in FIG. 6, in comparison with FITC-CPP$_{ecp}$ monomer (FIG. 6A), the FITC-CPP$_{ecp}$-dimer shared the same features of cell binding and penetration, and intracellular peptide localization was observed in cell surface, cytoplasm and nucleus in A549 cells, and this result indicates that the native functionalities of CPP$_{ecp}$ were not altered after disulfide bond formation (FIG. 6B).

EXAMPLE 4

Heparan Sulfate Binding Specificity of $CPP_{ecp}$-dimer

Cell culture

NCI-H460 cells were cultured in complete RPMI 1640 medium supplemented with heated inactivated 10% (v/v) fetal bovine serum (FBS) (Gibco), and 1% (v/v) of penicillin-streptomycin (Gibco). Cells were grown on 15-mm coverslips and incubated at 37° C. in 5% $CO_2$.

Heparan Sulfate Binding Assay

In order to certify if the specific binding affinity to heparan sulfate of disulfide linked $CPP_{ecp}$-dimer is still maintained as original $CPP_{ecp}$, the heparan sulfate binding affinity was investigated by FITC-conjugated $CPP_{ecp}$ monomer and dimer, and measured by fluorescence spectrophotometer. Lung carcinoma cells, NCI-H460 cells ($2*10^4$/well), were seeded into 96-well plate and incubated overnight. After complete adhesion, culture medium was removed and each well was blocked with 2% of BSA (1× PBS) at 4° C. for 1 hour to prevent non-specific binding. After blocking, each well was rinsed with 100 µl of cold 1× PBS to remove residual BSA. The FITC-conjugated peptide stocks ($CPP_{ecp}$ monomer and dimer) were prepared in $ddH_2O$ (100 µM) and added into each well (5 µl+95 µl serum-free medium) with desired concentrations, incubated at 4° C. for 1 hour. After binding, media with unbound peptides were removed and transferred to another plate. Each well was rinsed with 100 µl of 1× PBS and the rinse buffer was transferred to the second plate. After rinse, each well was refilled with 100 µl of 1× PBS and the fluorescence intensity was measured by fluorescence spectrophotometer (excitation: 485 nm; emission: 521 nm) as binding partition. Unbound and rinsed out peptides were obtained by adding up the fluorescence intensity of culture medium and buffer. In order to validate if the binding specificity of $CPP_{ecp}$ is heparan sulfate-dependent, before BSA blocking, cells were incubated with 5 U/ml of heparanase mixture (SIGMA) at 37° C. for 2 hours to remove cell surface heparan sulfate. After enzymatic treatment, each well was rinsed with 100 µl of 1× PBS to remove residual heparanase mixture and continued binding procedure as described above.

Figure 7:
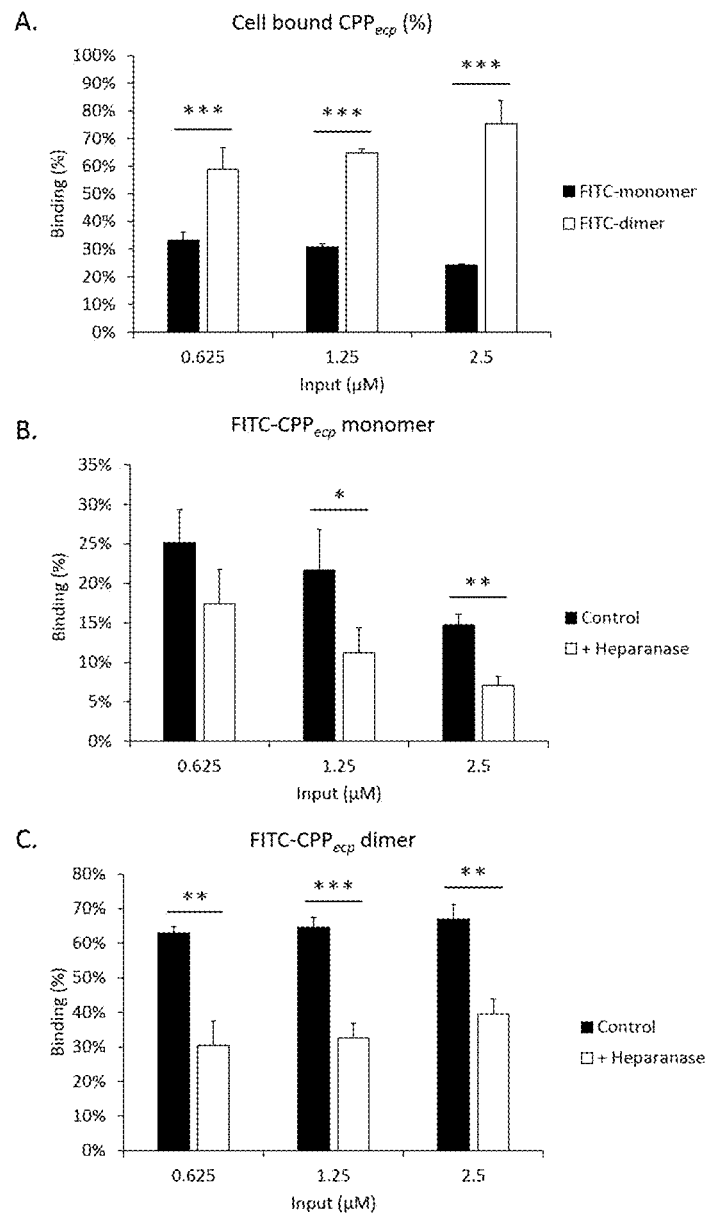
FIG. 7 illustrates binding specificity of $CPP_{ecp}$ and $CPP_{ecp}$-dimer on NCI-H460 cells. Before treatment, each well (96-well plate) was blocked by 2% of BSA at 4° C. for 1 hour, and washed with PBS once. After blocking, NCI-H460 cells were incubated with 0.625, 1.25 and 2.5 μM of FITC-$CPP_{ecp}$ and FITC-$CPP_{ecp}$ dimer at 4° C. for 1 hour. After washing with PBS, the binding of FITC-$CPP_{ecp}$ and FITC-$CPP_{ecp}$ dimer were measured by fluorescence spectrophotometer (A). To test binding specificity, cells were incubated with heparanase (5 U/ml) at 37° C. for 2 hours before peptide incubation (B and C). Total peptide inputs (binding and washout) were set as 100 percent and the relative binding of FITC-$CPP_{ecp}$ and FITC-$CPP_{ecp}$ dimer were calculated. The data represented the means of triplicate incubations. The error bars showed standard deviations among triplicate experiments.

Total peptide inputs (binding and washout) were calculated based on standard curves of each peptide. The binding percentage of FITC-$CPP_{ecp}$ and FITC-$CPP_{ecp}$-dimer were calculated based on the binding contents divided by total input. The data represented the means of triplicate incubations. The error bars showed standard deviations among triplicate experiments. As shown in FIG. 7A, in comparison with FITC-$CPP_{ecp}$ (monomer), the binding capacity of FITC-$CPP_{ecp}$dimer was significantly increased, which suggested the increase of binding ability after dimerization. For further confirm if these bindings are heparan sulfate dependent, heparanase was treated in NCI-H460 cells. As shown in FIG. 7C, decreased binding percentage of FITC-$CPP_{ecp}$-dimer was detected, as same as the trend showed in FITC-$CPP_{ecp}$ monomer (FIG. 7B). In conclusion, FITC-$CPP_{ecp}$-dimer shows better binding affinity to cells than FITC-$CPP_{ecp}$ and this binding is also through the heparan sulfate as FITC-$CPP_{ecp}$ did.

EXAMPLE 5

$CPP_{ecp}$-dimer as a Potential Drug Carrier

Figure 8:
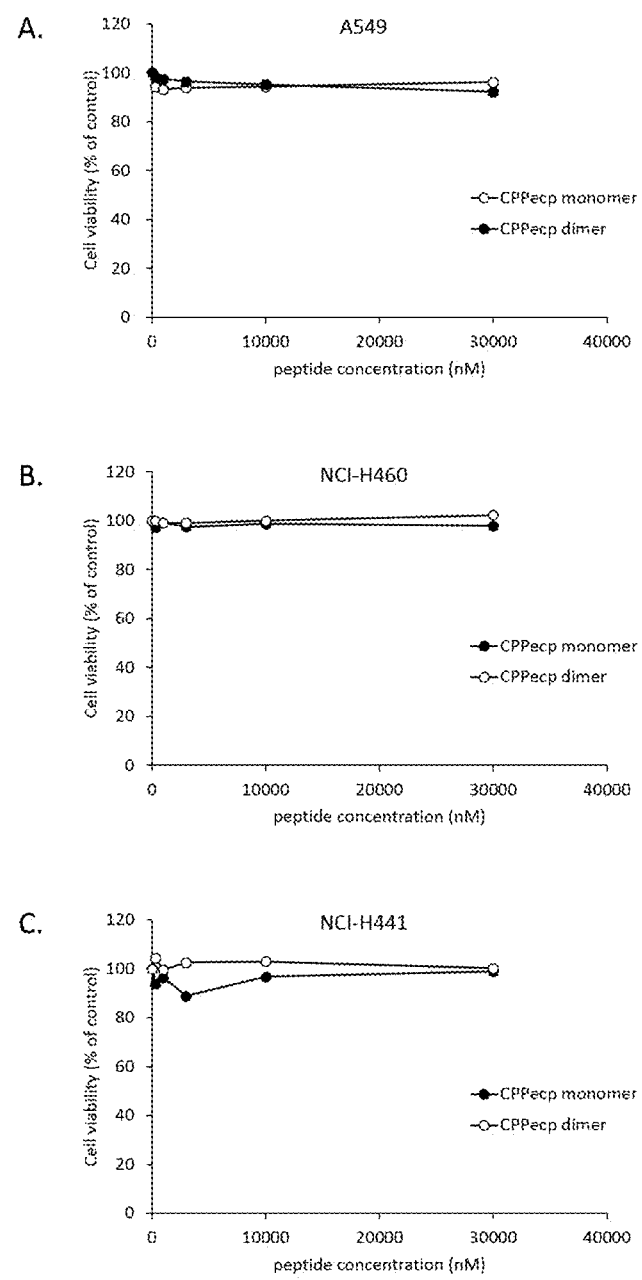
FIG. 8 illustrates toxicities of $CPP_{ecp}$ and $CPP_{ecp}$-dimer in different lung cancer cell lines. Cells were incubated with $CPP_{ecp}$ and $CPP_{ecp}$-dimer in different concentrations (0, 0.3, 1, 3, 10 and 30 μM) at 37° C. for 72 hours. Cell viabilities were measured by MTS assay. The 0 μM of $CPP_{ecp}$ (vehicle control) was set as 100 percent and the relative viabilities in each concentration were calculated.

In order to investigate the application potential of $CPP_{ecp}$-dimer as a drug carrier, the toxicity of $CPP_{ecp}$-dimer was tested and $CPP_{ecp}$ monomer was compared in three lung cancer cell lines: A549, NCI-H460 and NCI-H441. Lung cancer cell lines were seeded in 96-well plates ($2*10^3$/well) and incubated overnight. After adhesion, cells were incubated with different concentrations of $CPP_{ecp}$ and $CPP_{ecp}$ dimer (0, 0.3, 1, 3, 10 and 30 µM) for 72 hours. Cell viabilities were determined by MST assay (Promega Corp.). The cells without treatment were set as control and 100 percent and the relative viabilities in each concentration were calculated. As the results shown in FIG. 8, both $CPP_{ecp}$ monomer and $CPP_{ecp}$-dimer show no inhibitory effect on cell viabilities.

In summary, as the results shown in the invention, the stability of $CPP_{ecp}$ was improved by forming $CPP_{ecp}$ dimer through disulfide linkage between two $CPP_{ecp}$ molecules. This $CPP_{ecp}$-dimer still maintained the cell penetration as $CPP_{ecp}$, increased heparan sulfate binding affinity and showed no cellular toxicity, which suggests the potency for future medical applications. Furthermore, $CPP_{ecp}$-dimer also contributes the possibility of conjugating different therapeutic agents, diagnostic probes, or other small molecules to one carrier for the requirements of single or combinational therapy. Thus, the advantage of the present invention is able to be applied in combinational therapy or theranostics.

The above-mentioned descriptions represent merely the exemplary embodiment of the present invention, without any intention to limit the scope of the present disclosure thereto. Various equivalent changes, alternations or modifications, such as the polymer consisted of multiple cell penetrating peptides (multiple means bigger than or equal to two), based on the claims of present invention are all consequently viewed as being embraced by the scope of the present invention.

It will be understood that the above description of embodiments is given by way of example only and that various modifications may be made by those with ordinary skill in the art. The above specification, examples, and data provide a complete description of the present invention and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A polymer made by multiple cell penetrating peptides, each peptide comprising of $NYBX_1BX_2BNQX_3$ (SEQ ID NO: 1), wherein B represents a basic amino acid, $X_1$ represents an amino acid with an aromatic, a hydrophobic or an uncharged side chain, $X_2$ represents Cysteine, and $X_3$ represents Asparagine or none, and every the cell penetrating peptide is connected with each other by disulfide bond.

2. The polymer as defined in claim 1, wherein the polymer is cell penetrating peptide dimer.

3. The polymer as defined in claim 1, wherein the polymer has heparan sulfate binding activity.

4. The polymer as defined in claim 1, wherein every the cell penetrating peptide is connected with each other to form disulfide linkage by oxidative modification.

5. The polymer as defined in claim 4, wherein oxidative modification is able to be processed by adding an oxidizing agent.

6. The polymer as defined in claim 5, wherein the oxidizing agent is $H_2O_2$ or $CuSO_4$.

7. A complex comprising the polymer of claim 1 and a cargo selected from the group consisting of therapeutic agents, diagnostic probes, peptides, nucleic acids, antisense oligonucleotides, proteins, nanoparticles, liposomes, small molecules and radioactive materials.

8. A method for intracellular delivery, comprising: (a) providing a complex including the cell penetrating peptide of claim 1; and (b) culturing the complex with a targeted cell.

9. The method as defined in claim 8, wherein the complex comprises a cargo selected from the group consisting of therapeutic agents, diagnostic probes, peptides, nucleic acids, antisense oligonucleotides, proteins, nanoparticles, liposomes, small molecules and radioactive materials.

* * * * *

SEQUENCE LISTING

<160> NUMBER OF SEQ ID NOS: 2

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Generic
      Cell Penetrating Peptide Sequence -continued

```
<220> FEATURE:
<221> NAME/KEY: TRANSMEM
<222> LOCATION: 3
<223> OTHER INFORMATION: Xaa represents a basic amino acid
<220> FEATURE:
<221> NAME/KEY: TRANSMEM
<222> LOCATION: 4
<223> OTHER INFORMATION: Xaa represents an amino acid with an aromatic,
      a hydrophobic or an uncharged side chain
<220> FEATURE:
<221> NAME/KEY: TRANSMEM
<222> LOCATION: 5,7
<223> OTHER INFORMATION: Xaa represents a basic amino acid
<220> FEATURE:
<221> NAME/KEY: TRANSMEM
<222> LOCATION: 10
<223> OTHER INFORMATION: Xaa represents Asparagine or None

<400> SEQUENCE: 1

Asn Tyr Xaa Xaa Xaa Cys Xaa Asn Gln Xaa
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 2

Asn Tyr Arg Trp Arg Cys Lys Asn Gln Asn
1               5                   10
```